United States Patent [19]

Parisi

[11] Patent Number: 4,691,725
[45] Date of Patent: Sep. 8, 1987

[54] LENS CLEANER

[75] Inventor: Tulio T. Parisi, San Diego, Calif.

[73] Assignee: Ultramed Corporation, San Diego, Calif.

[21] Appl. No.: 732,926

[22] Filed: May 13, 1985

[51] Int. Cl.[4] .............................................. B08B 3/12
[52] U.S. Cl. ...................................... 134/184; 134/1; 206/5.1; 366/111; 366/127
[58] Field of Search ...................... 134/1, 25.4, 32, 34, 134/117, 137, 140, 143, 184, 196; 366/110, 111, 112, 114, 115, 127; 422/300, 301; 206/5.1

[56] References Cited

U.S. PATENT DOCUMENTS

| | | | |
|---|---|---|---|
| 2,724,393 | 11/1955 | Heise | 134/184 X |
| 3,169,538 | 2/1965 | Arnaudin | 134/143 X |
| 3,460,552 | 8/1969 | Sturgeon | 134/143 X |
| 3,512,539 | 5/1970 | Hamilton | 134/140 X |
| 3,614,959 | 10/1971 | Schollmaier et al. | 134/117 |
| 3,880,278 | 4/1975 | Brown | 134/137 X |
| 4,458,705 | 7/1984 | Cawood | 134/137 X |

FOREIGN PATENT DOCUMENTS 94325 7/1981 Japan ..................... 206/5.1

Primary Examiner—Philip R. Coe
Attorney, Agent, or Firm—Ellsworth R. Roston; Charles H. Schwartz

[57] ABSTRACT

A housing supports a tray for slidable movement of the tray within the housing. The tray and the housing may be paramagnetic. The tray is shaped to define at least one cup for receiving a contact lens and cleaning fluid. The tray may be supported on a resiliently compressible pad which is in turn supported on a ledge forming a part of the housing. A slug is supported by, or embedded in, the tray to provide for a movement of the slug with the tray. The slug may be magnetizable and may be displaced from an armature and a coil enveloping the armature. When the coil is energized, it magnetizes the armature. The energizing of the armature causes the slug to be attracted to the armature in a direction to compress the pad. When the coil is de-energized, the compressed pad expands to move the tray away from the armature. In this way, the tray is vibrated in directions to displace the contact lens from the wall of the cup and to agitate the cleaning fluid so that all of the surfaces of the contact lens are cleaned. The vibrations may occur at frequencies below the frequencies of sound or in the ultrasonic range.

13 Claims, 5 Drawing Figures

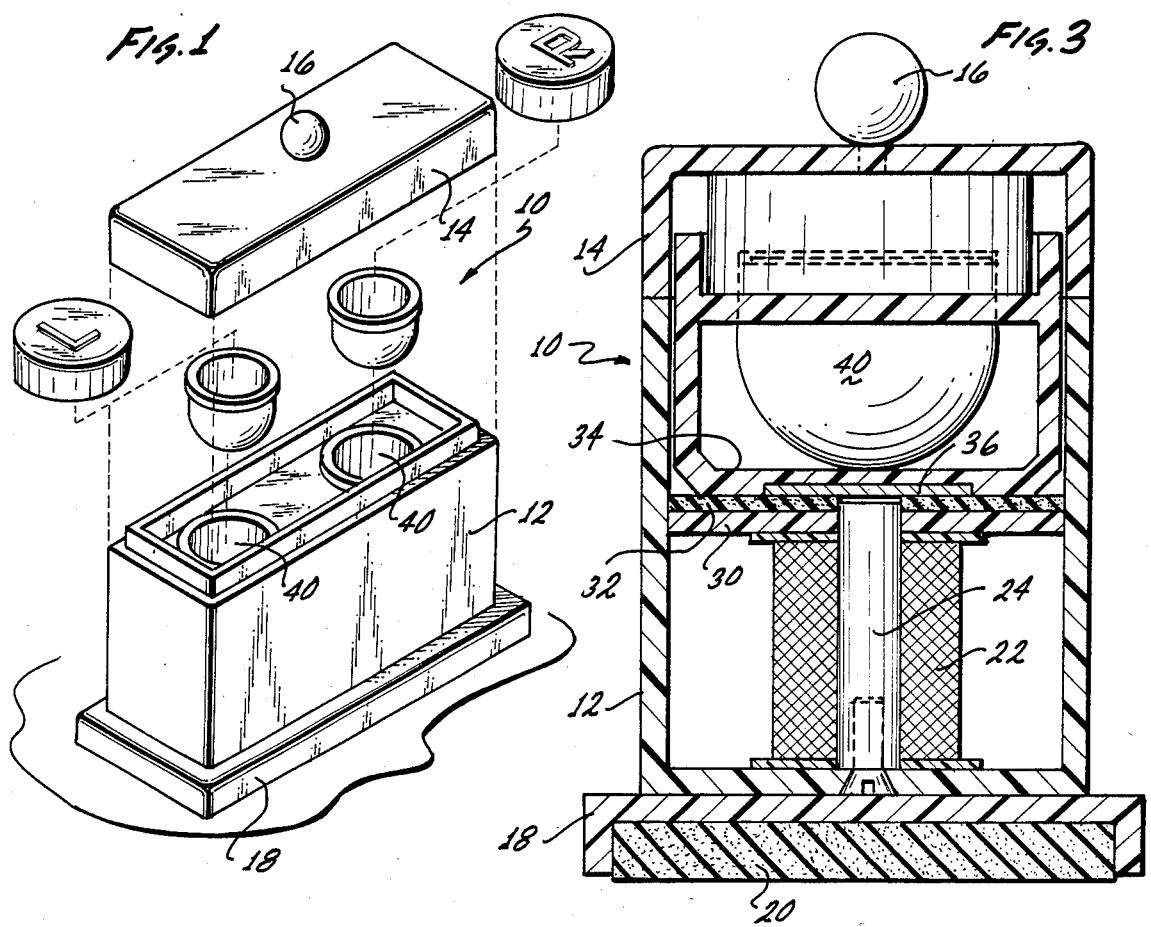
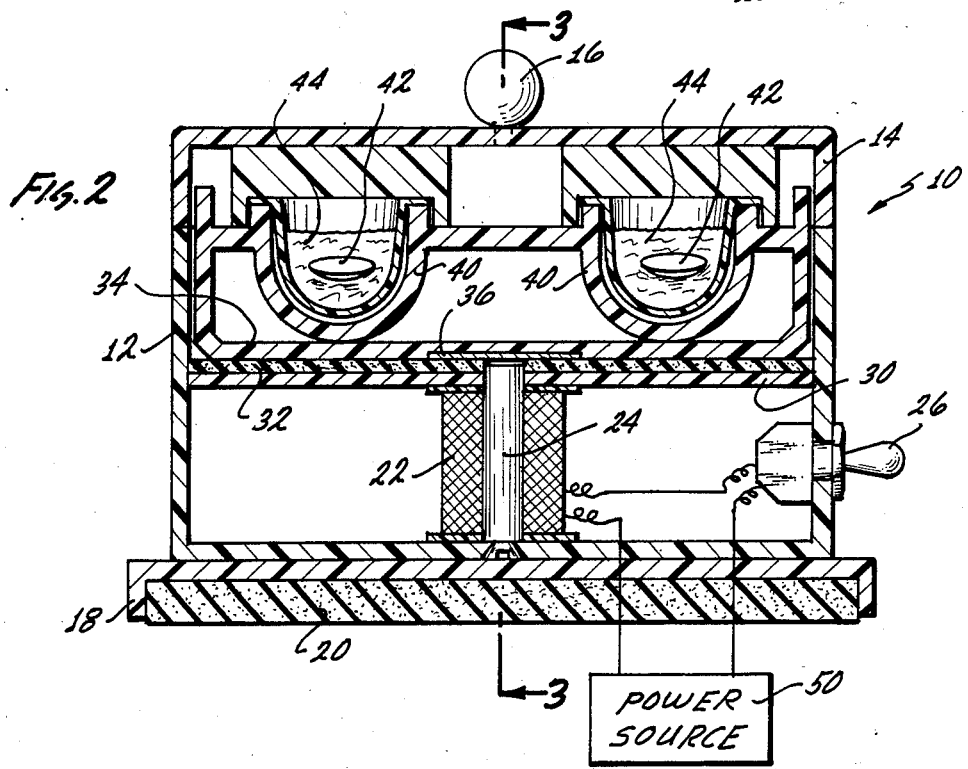

LENS CLEANER

This invention relates to apparatus for cleaning contact lenses. The invention further relates to apparatus which cleans such lenses efficiently without damaging the lenses.

Contact lenses are now being worn by millions of people. They provide enhanced vision to the wearers and at the same time provide convenience to those who tend to misplace articles. The contact lenses also increase the confidence of those people who believe that eyeglasses detract from their looks.

Since contact lenses are disposed in the eye, they should be clean and sterile. It is accordingly important that the lenses be cleaned, and even sterilized, before they are placed in the wearer's eyes. It is further important that the cleaning be accomplished simply and efficiently. It is further important that the cleaning does not scratch the lenses since scratches in the lenses mar the vision of the wearer.

Since contact lenses have been in existence for a number of years, efforts have been made to provide cleaning apparatus which will meet the tests specified in the previous paragraph. Such efforts have been extensive because of the substantial use by the populace of contact lenses. In spite of such efforts, satisfactory cleaning apparatus for lenses still does not exist. For example, the apparatus now in use does not provide a satisfactory cleaning operation. Furthermore, it tends to scratch the lenses, and tear them.

This invention provides apparatus which meets the standards above. For example, the apparatus of this invention cleans lenses efficiently without scratching the lenses. The apparatus of this invention is simply constructed with a minimal number of parts so that it can be constructed and sold inexpensively and so that it will operate reliably over extended periods of time without having to be repaired.

In one embodiment of the invention, a housing supports a tray for slidable movement of the tray within the housing. The tray and the housing may be paramagnetic. The tray is shaped to define a cup for receiving a contact lens and cleaning fluid. The tray may be supported on a resiliently compressible pad which is in turn supported on a ledge forming a part of the housing.

A slug is supported by, or embedded in, the tray to provide for a movement of the slug with the tray. The slug may be magnetizable and may be displaced from an armature and a coil enveloping the armature. When the coil is energized, it magnetizes the armature. The energizing of the armature causes the slug to be attracted to the armature in a direction to compress the pad. When the coil is de-energized, the compressed pad expands to move the tray away from the armature.

In this way, the tray is vibrated in directions to displace the contact lens from the wall of the cup and to agitate the cleaning fluid so that all of the surfaces of the contact lens are cleaned. The vibrations may occur at frequencies below the frequencies of sound or in the ultrasonic range.

In the drawings:

FIG. 1 is an exploded perspective view of apparatus constituting the embodiment of this invention for cleaning lenses;

FIG. 2 is an enlarged vertical section of the cleaning apparatus shown in FIG. 1;

FIG. 3 is a sectional view of the cleaning apparatus shown in FIGS. 1 and 2 and is taken substantially on the line 3—3 of FIG. 2;

Figure 4:
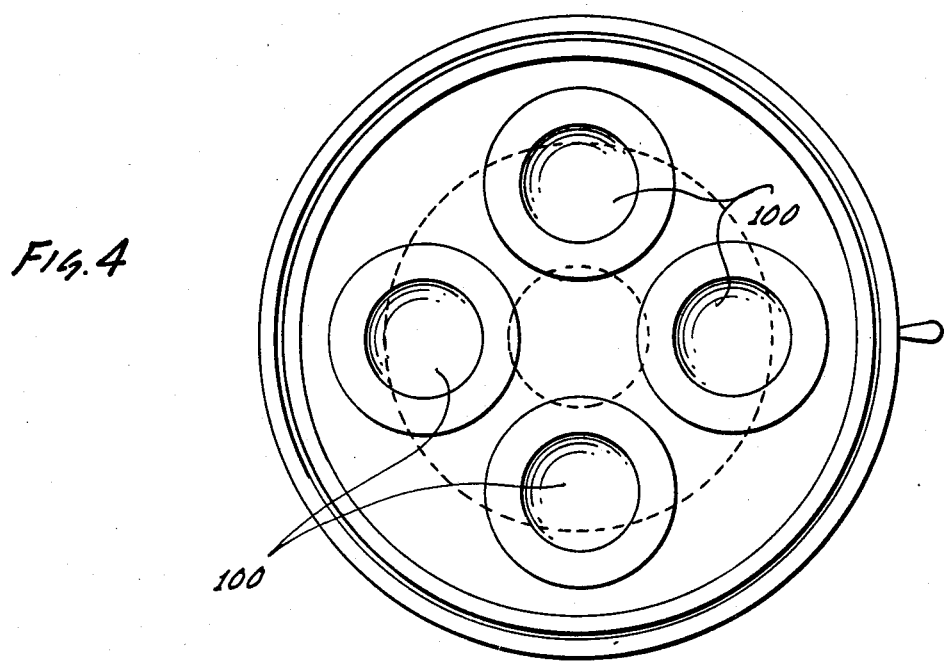
FIG. 4 is a top plan of a modification of the embodiment of the invention shown in FIGS. 1, 2 and 3.

In one embodiment of the invention, cleaning apparatus generally indicated at 10 is provided. The cleaning apparatus 10 includes a housing 12 and a cover 14 for the housing, the cover having a knob 16. The housing 12, the cover 14 and the knob 16 are preferably made from a suitable non-magnetic material such as a plastic. The housing 12 is attached to a hollow base 18 which also can be made from a suitable material such as a plastic. A resilient material 20 made from a suitable material such as rubber is disposed within the base 18 to cushion any vibration of the housing 12.

A coil 22 is supported on the bottom wall of the container 12. The coil 22 envelopes an armature 24 made from a suitably magnetizable material such as iron. The armature 24 is fixedly positioned at its bottom end relative to the bottom wall of the housing 12. The coil 22 is energized when a switch 26 is closed. The switch 26 is supported on a side wall of the housing 12.

A support plate 30 is disposed above the coil 22 at an intermediate position between the top wall of the cover 14 and the bottom wall of the housing 12. A resilient pad 32 made from a suitable material such as foam rubber is disposed on the support plate 30. A tray 34 is in turn supported on the pad 32 for slidable movement relative to the vertical walls of the housing 12. The support plate 30 and the tray 34 may be made from a suitable non-magnetic material such as a plastic. A slug 36 made from a suitable magnetizable material such as iron is embedded in the bottom wall of the tray 34 at a position directly above the armature 34.

The tray 34 is shaped to define a pair of spaced cups 40 for receiving lenses 42. A cleaning fluid 44 may be disposed in the cups 40. Caps 46 made from a non-magnetic material such as a plastic material are adaped to be disposed on the cups 40 to close the cups so that the cleaning fluid 44 cannot spill from the cups and the lenses 42 cannot fall from the cups. The bottoms of the cups 40 are preferably integral with the bottom wall of the tray 34 to impart strength and rigidity to the cups.

The switch 26 is connected to a source 50 of electrical pulses. When the switch 26 is closed, the coil 22 is energized and magnetic flux is produced in the armature 24. This magnetic flux attracts the slug 36 so that the tray 34 moves downwardly to compress the pad 32. Upon a subsequent de-energizing of the coil 22, the tray 34 is moved upwardly by the pad 32 to relieve the compression in the pad.

The tray 34 accordingly vibrates vertically at the same frequency as the pulses from the source 50. These pulses may be produced at a suitable frequency such as approximately sixty (60) hertz per second or at frequencies in the ultrasonic range.

The vibrations of the tray 34 produce vibrations in the cleaning fluid 44 in the cups 40. These vibrations in turn produce a cleaning action on the contact lenses 42. Since the vibrations occur vertically, the lenses 42 tend to float in the cleaning fluid 44. As a result, the cleaning fluid 44 tends to clean all of the surfaces of the contact lenses 42 without scratching or otherwise marring the surfaces of the lenses.

The apparatus described above has certain important advantages. It is simple in construction and reliable in operation. It provides an efficient cleaning of contact lenses without scratching or otherwise marring the surfaces of the lenses. The apparatus accordingly has wide utility to the considerable segment of the population wearing contact lenses.

Figure 5:
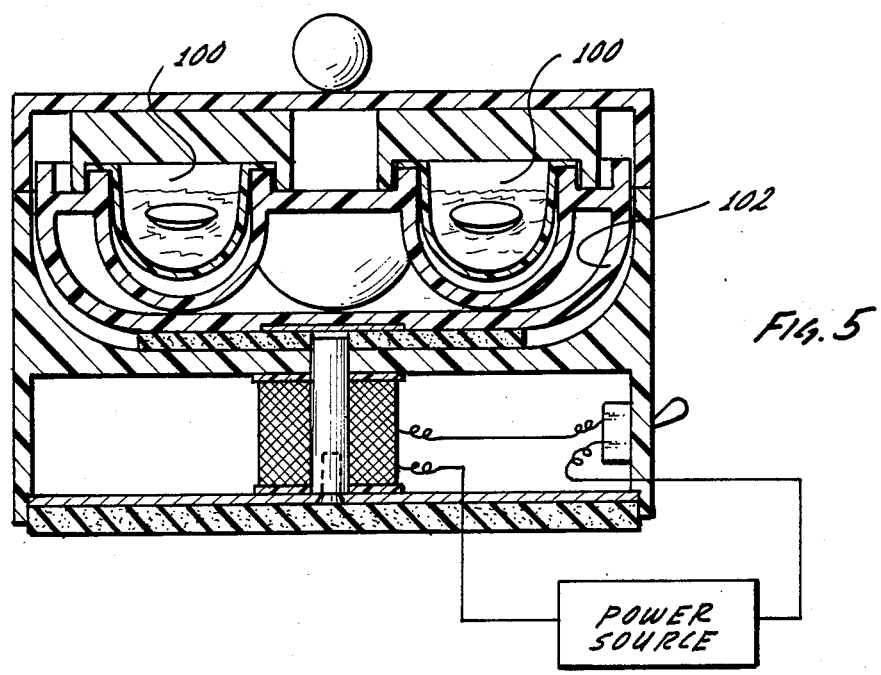
FIG. 5 is a vertical section of the modification shown in FIG. 4 and is taken substantially on the same line as in FIG. 2.

FIGS. 4 and 5 illustrate a modification of the embodiment shown in FIGS. 1, 2 and 3 and described above. In the embodiment shown in FIGS. 4 and 5, four lens cups 100 are provided in a tray 102 corresponding to the tray 34 in FIGS. 1, 2 and 3. Two (2) of the lens cups 100 are provided for washing and soaking the contact lens during the vibrations of the tray. The other two (2) of the lens cups 100 are provided to rinse the lenses during the vibrations of the tray. After the lenses have been rinsed, they are ready to be inserted into the wearer's eyes.

Although this invention has been disclosed and illustrated with reference to particular embodiments, the principles involved are susceptible for use in numerous other embodiments which will be apparent to persons skilled in the art. The invention is, therefore, to be limited only as indicated by the scope of the appended claims.

I claim:

1. In combination for cleaning a contact lens with a cleaning fluid,
   a housing,
   means disposed in the housing in displaceable relationship to the housing for holding the contact lens and the cleaning fluid,
   means disposed in the housing for producing electrical pulsations,
   means responsive to the electrical pulsations for vibrating the holding means relative to the housing to obtain a movememt of the contact lens relative to the holding means and the cleaning fluid and to obtain a cleaning of the contact lens by the cleaning fluid during such movement, and
   resilient support means for the holding means, and
   means responsive to the electrical pulsations for pressing the holding means against the resilient support means during the production of the electrical pulsations and for providing for the release of the pressure of the holding means against the resilient support means during the period of time between successive electrical pulsations.

2. A combination as set forth in claim 1, including,
   magnetizable means supported by the housing and responsive to the electrical pulsations for providing for the displacement of the holding means against the resilient support means in accordance with the production of the electrical pulsations.

3. In combination for cleaning a contact lens with a cleaning fluid,
   means for holding the lens and the cleaning fluid,
   enclosure means retaining the holding means in movable relationship to the enclosure means,
   a resilient pad for supporting the holding means,
   magnetizable means coupled to the holding means for displacement of the holding means against the resilient pad, and
   means disposed relative to the magnetizable means for alternately producing and releasing a magnetizable force on the magnetizable means in a direction to press the holding means against the resilient pad and release the holding means from the resilient pad for the production of vibrations in the cleaning fluid and the provision of a floating relationship of the contact lens in the fluid to obtain a cleaning of substantially all of the surfaces of the contact lens by the cleaning fluid.

4. A combination as set forth in claim 3, including,
   the means for producing the magnetizable force including a coil for producing an electrical current and an armature disposed relative to the coil to become energized by the coil for the production of a magnetic field, the magnetizable means being displaced from the armature and being disposed in the magnetic field to become displaced upon the production of the magnetizable field in a direction for pressing against the resilient pad.

5. A combination as set forth in claim 4, including,
   the holding means defining a cup, and
   a cap on the cup for closing the cup to prevent the cleaning fluid from spilling from the cup.

6. In combination for cleaning a contact lens with a cleaning fluid,
   a housing,
   a removable cover for the housing,
   a tray supported in the housing in slidable relationship to the housing, the tray being shaped to define a cup for holding the contact lens and the cleaning fluid,
   a resilient pad supported on the housing in abutting relationship to the tray for compression by the tray, and
   means operatively coupled to the tray for alternately obtaining a sliding movement of the tray relative to the housing in a direction to compress the pad and then release this compression for the production of vibrations in the cup.

7. A combination as set forth in claim 6, including,
   means for producing an electrical current,
   the moving means being responsive to the electrical current for producing a magnetic field and the tray being constructed to be responsive to the magnetic field for displacement in a direction to compress the resilient pad.

8. A combination as set forth in claim 7 including,
   the tray supporting a magnetizable slug for movement with the tray, the slug being disposed in the magnetic field to become attracted by the magnetic field for displacement in a direction to compress the resilient pad.

9. A combination as set forth in claim 8, including,
   a removable cap on the cup.

10. In combination for cleaning a contact lens with a cleaning fluid,
    a housing,
    holding means disposed in the housing in slidable relationship to the housing, the holding means being shaped to define a cup for holding the contact lens and the cleaning fluid,
    resiliently compressible means supporting the holding means in the housing for alternate compression and release of compression of the resiliently compressible means by the holding means, and
    means operable on the holding means for producing alternate displacements of the holding means in the enclosure in directions to compress the compressible means and release the compression on the compressible means.

11. A combination as set forth in claim 10, including,
    the displacement means being magnetizable and demagnetizable and including a member supported by the holding means for producing a movement of the holding means in a first direction, when magnetized, to compress the compressible means and for providing for a movement of the holding means in a second direction opposite to the first direction when the member is demagnetized.

12. A combination as set forth in claim 11, including, means including a coil energizable to produce a magnetic field,
the magnetizable member being within the magnetic field produced by the coil when the coil is energized.

13. A combination as set forth in claim 11, including, a removable cover for the housing,
the housing and the cover being made from a paramagnetic field.

* * * * *